(12) United States Patent
Laurents et al.

(10) Patent No.: US 6,891,076 B2
(45) Date of Patent: May 10, 2005

(54) PROCESS FOR THE RECOVERY OF PERFLUORINATED SULPHONIC ACIDS FROM SPENT ACID RESIDUE

(75) Inventors: Karsten Laurents, Lyngby (DK); Ole Stahl, Lynge (DK)

(73) Assignee: Haldor Topsoe A/S, Lyngby (DK)

( * ) Notice: Subject to any disclaimer, the term of this patent is extended or adjusted under 35 U.S.C. 154(b) by 481 days.

(21) Appl. No.: 10/144,709

(22) Filed: May 15, 2002

(65) Prior Publication Data
US 2003/0004388 A1 Jan. 2, 2003

(30) Foreign Application Priority Data
May 19, 2001 (DK) .......................................... 2001 00809

(51) Int. Cl.[7] ................................................. B01J 38/60
(52) U.S. Cl. ...................... 585/712; 585/719; 585/721; 502/26; 502/27
(58) Field of Search ............................... 585/712, 719, 585/721; 502/26, 27

(56) References Cited

U.S. PATENT DOCUMENTS

| | | | |
|---|---|---|---|
| 5,603,812 A | * | 2/1997 | Hommeltoft ................. 203/29 |
| 5,618,769 A | * | 4/1997 | Hommeltoft ................. 502/26 |
| 5,759,357 A | * | 6/1998 | Hommeltoft ................. 203/29 |

FOREIGN PATENT DOCUMENTS

| | | |
|---|---|---|
| EP | 1 044 963 A2 | 10/2000 |
| EP | 1 065 199 A2 | 1/2001 |

* cited by examiner

Primary Examiner—Walter D. Griffin
Assistant Examiner—Tam M. Nguyen
(74) Attorney, Agent, or Firm—Dickstein Shapiro Morin & Oshinsky, LLP

(57) ABSTRACT

Process for the recovery of perfluorinated sulphonic acid from a hydrocarbon residue, comprising the steps of
(a) treating the residue with an alkyl ammonium salt of the perfluorinated sulphonic acid or a mixture of an alkyl ammonium salt of the perfluorinated sulphonic acid and the perfluorinated sulphonic acid in an amount being effective to liquefy the residue at ambient temperature;
(b) contacting the liquefied residue with water at conditions to obtaining an aqueous extract containing the perfluorinated sulphonic acid and/or the alkyl ammonium salt of the perfluorinated acid into water; and
(c) separating water from the aqueous extract to recover the perfluorinated sulphonic acid or the mixture of the acid and the ammonium salt.

6 Claims, 1 Drawing Sheet

Figure 1:
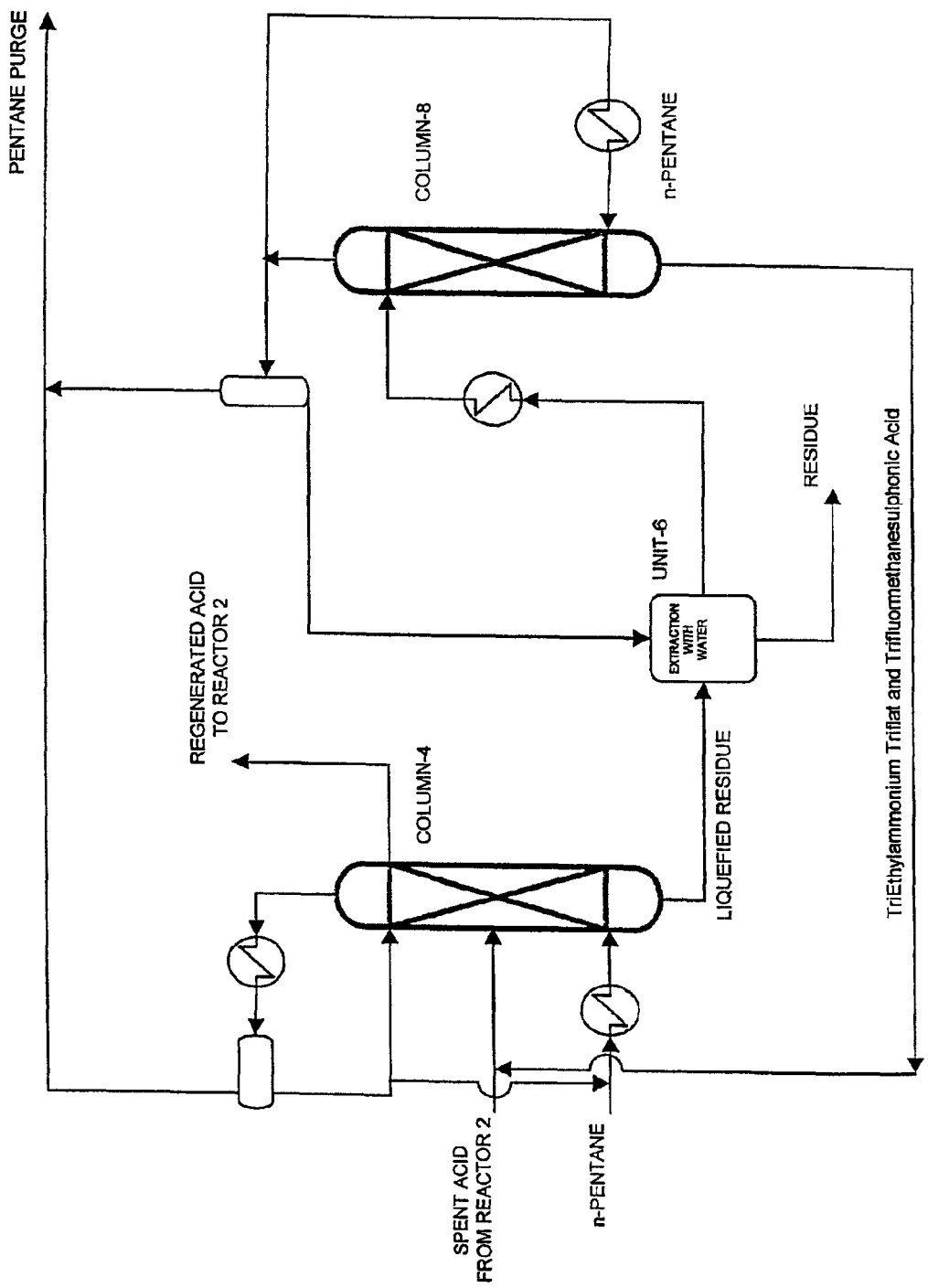

PROCESS FOR THE RECOVERY OF PERFLUORINATED SULPHONIC ACIDS FROM SPENT ACID RESIDUE

The present invention relates to a process for the recovery of perfluorinated sulphonic acid from a hydrocarbon residue. In particular, the invention provides recovery of those acids from spent acid residue by extraction including steps of diluting the spent acid residue with the acid or a mixture of an alkyl ammonium salt of the acid and the acid to obtain a liquid from which the extraction of acid with water is facilitated.

EP Patent No. 1,044,963 A describes a process in which spent acid from an alkylation process is processed in a stripping column with the result that fresh, regenerated acid is obtained as a top product along with a hydrocarbon product originating from cracking of the organic part of spent acid. Spent acid residue resulting from the stripping process described in this patent publication is typically a highly viscous liquid containing mainly higher aromatic hydrocarbons and acid. Depending on the severity of the spent acid stripping operation, the spent acid residue can be solid at room temperature and as such, the residual acid is difficult to extract from the residue.

Furthermore, it is known that residue can be dissolved in solvents such as anisol and residual acid can be extracted with water from such a mixture. However, due to density of anisol being close to that of water, phase separation is a troublesome operation. Depending on the acid concentration in the aqueous phase, this phase can be more or less dense than the organic phase thereby causing problems with phase inversion in automated continuous phase separation processes.

It was previously observed that addition of certain co-solvents to hydrocarbon residue decreases the organic phase density and leaves this phase less dense than the aqueous phase. Solvents such as THF have been found to be efficient co-solvents.

Uses of solvents, which are not directly needed in the acid regeneration process, are undesirable due to the added complexity of the overall process when solvent regeneration is included. From a process standpoint it is desirable to recover residual amounts of acid from spent acid residue without addition of further solvents.

EP Patent No. 1,065,199 A describes a process by which acid is stripped from a mixture of acid and an alkyl ammonium salt of the acid in a stripping column with the result that fresh, regenerated acid is obtained as a top product. It has now been found that spent acid residue from the stripping column is mixable with alkyl ammonium salts of the acid and that the resulting mixture is liquid at room temperature, which reduces the complexity of handling, storing and further processing of the residue.

Furthermore, it was observed that sufficient amounts of alkyl ammonium salt added to the residue result in precipitation of a fine powder of hydrocarbon residue when contacting the mixture with water to extract residual amounts of acid. Alkyl ammonium salt of the acid can be mixed with the spent acid prior to introduction into a stripping column, thus reducing plugging of the bottom exit system of the stripping column especially in up-set situations. Thereby, it is possible to combine the stripping process described in EP Patent No. 1,044,963 A with the process described in EP Patent No. 1,065,199 A and performing the two processes in a single stripping column. Spent acid regeneration is in a further embodiment of the invention obtained by mixing spent acid from an alkylation process with a mixture of a corresponding acid and an alkyl ammonium salt of the acid as further explained in more detail in the following description with reference to FIG. 1 in the attached drawing.

FIG. 1 represents a simplified flow sheet of an acid recovery process according to the invention for the recovery of trifluoromethanesulphonic acid catalyst from spent acid formed in alkylation of paraffinic hydrocarbons with olefinic alkylation agent in presence of the above acid catalyst.

Spent acid from alkylation reactor 2 is passed to spent acid stripping column 4. Prior to introduction into stripping column 4, the spent acid is admixed with a mixture of trifluoromethanesulphonic acid and triethyl ammonium triflate from a down stream acid/salt stripping column 8 as further described below. In stripping column 4 trifluoromethanesulphonic acid contained in the spent acid is stripped off by means of n-pentane and recycled to alkylation reactor 2. Stripping residue formed in column 4 is a highly viscous hydrocarbon mixture, which by addition of the acid/salt mixture to the spent acid is liquefied as described herein previously.

The residue contains valuable amounts of trifluoromethanesulphonic acid and ammonium trifalte, which are recovered by extraction with water in extraction unit 6. Water is separated for the acid/triflate mixture in stripping column 8 by stripping the aqueous mixture with n-pentane. Recovered acid/triflate mixture is then recycled to inlet of stripping column 4, as described above.

EXAMPLES

Example 1

A mixture of spent trifluoromethanesulphonic acid from an isobutane alkylation pilot plant containing 67.4 wt % trifluoromethanesulphonic acid, 30.6 wt % higher hydrocarbon by-products and 2.0 wt % water was mixed with 10 wt % trifluoromethanesulphonic acid in triethyl ammonium triflate. The resulting mixture contained 56.0 wt % trifluoromethanesulphonic acid, 24.5 wt % higher hydrocarbon by-products, 18.0 wt % triethyl ammonium triflate and 1.6 wt % water.

The mixture was charged at a feed rate of 575 g/h to top of a stripping column at a temperature of 50° C. The stripping column was a 0.6 m of a ID=32.5 mm tube filled with 150 ml 3*3 mm SS rings on top of 230 ml 6*6 mm glass rings and operated at atmospheric pressure. Stripping agent (n-pentane) was added at a feed rate of 855 g/h near bottom of the column at a temperature of 255° C.

Recovered trifluoromethanesulphonic acid was condensed overhead along with stripping agent and a hydrocarbon fraction substantially boiling in the gasoline range formed by cracking of higher hydrocarbon by-products from the spent acid. Spent acid residue containing triethyl ammonium triflate was removed from the bottom of the column.

| Spent acid feed rate, g/h | |
|---|---|
| Trifluoromethanesulphonic acid | 322 |
| Triethyl ammonium triflate | 104 |
| Higher hydrocarbon by-products Water | 141 |
| | 9 |
| Stripping agent feed rate, g/h | |
| Isopentane | 855 |
| Top product rate, g/h | |
| Trifluoromethanesulphonic acid | 288 |
| Gasoline range hydrocarbons | 91 |

-continued

| | |
|---|---|
| Water | 9 |
| Bottom product rate, g/h | |
| Trifluoromethanesulphonic acid | 34 |
| Triethyl ammonium triflate | 104 |
| Organic residue | 50 |
| Stripping agent temperature, ° C. | 255 |
| Column bottom temperature, ° C. | 215 |
| Column top temperature, ° C. | 170 |
| Cracking of spent acid higher hydrocarbon by-products, % | 65 |
| Recovery of trifluoromethanesulphonic acid in overhead, % | 90 |
| Viscosity of bottom product, Pa*s | 2986 |

Example 2

A number of samples were prepared in which varying amounts of stripper column residue and triethyl ammonium triflate were mixed. Theological behavior was determined for each sample using a rotational viscometer within the shear rate ranges $10^{-2}$–$10^3$ s$^{-1}$ (ISO 3219–93). Equipment used was a Bohlin Rheometer VOR 9:2 with standard geometry C25.

| Amount of residue and salt, wt:wt | Viscosity at 23° C., Pa*s |
|---|---|
| 1:0 | 4.2*10$^6$ |
| 1:1 | 3269 |
| 1:2 | 328 |
| 1:3 | 101 |
| 1:5 | 94 |

Example 3

Three experiments were performed in which trifluoromethanesulphonic acid in spent acid residue from stripping column 4 was extracted with water in a series of extraction steps.

In one experiment spent acid residue from a stripping operation without salt addition was contacted with 1 volume of water in each of 3 steps. Each step consisted of agitated heating to a temperature of 100° C. followed by cooling to 23° C. and separation of extract from residue by filtration. Samples of the residue after each extraction step were analysed for sulphur by elemental analysis and the total triflate concentration was calculated.

In a second experiment 1 part spent acid residue as above mixed with 3 parts 30 wt % trifluoromethanesulphonic acid in triethyl ammonium triflate was contacted with 1 volume of water in each of 3 steps. Each step consisted of agitated heating to a temperature of 100° C. followed by cooling to 23° C. and separation of extract from residue by filtration. Samples of the residue after each extraction step were analysed for sulphur by elemental analysis and the total triflate concentration was calculated.

A third experiment was conducted as the second except that no heating took place.

| | Total triflate in residue, wt % | | |
|---|---|---|---|
| Extraction step No. | Without salt, 100° C. | With salt, 100° C. | With salt, 25° C. |
| 0 | 32.3 | 32.3 | 32.3 |
| 1 | 23.4 | 11.4 | 15.4 |
| 2 | 20.3 | 4.4 | 14.0 |
| 3 | 17.8 | 2.1 | 13.7 |

What is claimed is:

1. Process for the recovery of perfluorinated sulphonic acid from a hydrocarbon residue, comprising the steps of
   (a) treating the residue with an alkyl ammonium salt of the perfluorinated sulphonic acid or a mixture of an alkyl ammonium salt of the perfluorinated sulphonic acid and the perfluorinated sulphonic acid in an amount being effective to liquefy the residue at ambient temperature;
   (b) contacting the liquefied residue with water at conditions to obtaining an aqueous extract containing the perfluorinated sulphonic acid and/or the alkyl ammonium salt of the perfluorinated acid into water; and
   (c) separating water from the aqueous extract to recover the perfluorinated sulphonic acid or the mixture of the acid and the ammonium salt.

2. Process according to claim 1, wherein the treatment of the hydrocarbon residue in step (a) is performed prior to stripping of the residue with a stripping agent.

3. Process according to claim 1, wherein the separation of water from the aqueous extract in step (c) is performed by stripping the extract with a stripping agent.

4. Process according to claim 1, comprising the further step of recycling the recovered perfluorinated sulphonic acid or the mixture of the acid and the ammonium salt from step (c) to step (a).

5. Process according to claim 2, wherein the stripping agent in step (a) is used as stripping agent in step (c).

6. Process according to claim 3, wherein the stripping agent in step (a) is used as stripping agent in step (c).

* * * * *